United States Patent [19]

Vogel

[11] 4,034,038

[45] July 5, 1977

[54] BORON-CONTAINING ESTERS

[75] Inventor: Paul W. Vogel, Lyndhurst, Ohio

[73] Assignee: The Lubrizol Corporation, Wickliffe, Ohio

[22] Filed: June 19, 1972

[21] Appl. No.: 264,094

Related U.S. Application Data

[63] Continuation of Ser. No. 885,265, Dec. 15, 1969, abandoned, which is a continuation-in-part of Ser. No. 800,367, Feb. 12, 1969, abandoned, which is a continuation of Ser. No. 323,266, Nov. 13, 1963, abandoned.

[52] U.S. Cl. .......................................... 260/462 R
[51] Int. Cl.² .......................................... C07F 5/04
[58] Field of Search .............................. 260/462 R

[56] References Cited
UNITED STATES PATENTS

| | | | |
|---|---|---|---|
| 1,668,797 | 5/1928 | Bannister | 260/639 B |
| 3,155,686 | 11/1964 | Prill et al. | 260/484 B |

*Primary Examiner*—Donald G. Daus
*Assistant Examiner*—D. B. Springer
*Attorney, Agent, or Firm*—James W. Adams, Jr.

[57] ABSTRACT

Boron-containing products useful as lubricant additives are obtained by reacting high molecular weight succinic acid-producing compounds with polyhydric alcohols and a boron reagent such as boric acid.

11 Claims, No Drawings

BORON-CONTAINING ESTERS

This application is a continuation of copending application Ser. No. 885,265 filed Dec. 15, 1969 abandoned, which, in turn, is a continuation-in-part of application Ser. No. 800,367, filed Feb. 12, 1969, the latter being a continuation of application Ser. No. 323,266, filed Nov. 13, 1963. Both of the latter applications are now abandoned. Earlier filed application Ser. No. 744,688 filed July 15, 1968, now U.S. Pat. No. 3,533,945, is a division of application Ser. No. 323,266.

This invention relates to novel compositions of matter and processes for preparing the same. In a more particular sense this invention relates to compositions useful as plasticizers, detergents, anti-rust agents, emulsifiers, and additives in lubricating compositions, fuels, hydrocarbon oils, and power transmitting fluids.

Deterioration of lubricating oils, especially mineral oils, has been a great concern in the formulation of lubricating compositions for use in internal combustion engines, transmissions, gears, etc. Deterioration of the oil results in the formation of products which are corrosive to the metal surfaces with which the oil comes into contact. It also results in the formation of products which agglomerate to form sludge and varnish-like deposits. The deposits cause sticking of the moving metal parts and obstruct their free movement. They are a principal cause of malfunctioning and premature break-down of the equipment which the oil lubricates.

It is known that water is a common contaminant in the crankcase lubricant of an engine. It may result from the decomposition of the lubricating oil or come from the combustion chamber of water in the lubricant seems to promote the deposition of a mayonnaise-like sludge. This type of sludge is more objectionable because it clings tenaciously to metal surfaces and is not removed by oil filters. If the engine is operated under conditions such that the crankcase lubricant temperature is continuously high the water will be eliminated about as fast as it accumulates and only a very small amount of the mayonnaise-like sludge will be formed. On the other hand, if the crankcase lubricant temperature is intermittently high and low or consistently low the water will accumulate and a substantial quantity of the mayonnaise-like sludge will be deposited in the engine.

High operating temperatures are characteristic of an engine that is run consistently at a relatively high speed. However, where an automobile is used primarily for trips of short distance such as is characteristic of urban, home to work use, a significant portion of the driving occurs before the engine has reached its optimum high temperature. An ideal environment thus obtains for the accumulation of water in the lubricant. In this type of operation the problem of mayonnaise-like sludge has been especially troublesome. Its solution has been approached by the use in the lubricant of detergents such as metal phenates and sulfonates which have been known to be effective in reducing deposits in engines operated primarily at high temperatures. Unfortunately, such known detergents have not been particularly effective in solving the problems associated with low temperature operation particularly those problems which are associated with crankcase lubricants in engines operated at low or intermittently high and low temperatures.

It is accordingly a principal object of this invention to provide novel compositions of matter.

It is also an object of this invention to provide compositions which are suitable for use as additives in hydrocarbon oils.

It is also an object of this invention to provide compositions which are effective as additives in lubricating compositions.

It is another object of this invention to provide compositions effective as detergents in lubricating compositions intended for use in engines operated at low or intermittently high and low temperatures It is another object of this invention to provide a process of preparing additives useful as additives in hydrocarbon oils and lubricating compositions.

It is another object of this invention to provide lubricating compositions.

It is further an object of this invention to provide fuel compositions.

These and other objects are attained in accordance with this invention by providing a process for preparing boroncontaining esters comprising the reaction of one mole of a polyhydroxy compound having the formula

wherein R is a hydrocarbon radical and $x$ is an integer representing the number of hydroxy radicals and has a value of from 2 to about 10 with (A) at least about 0.5 mole of a succinic acid-producing compound selected from the class consisting of hydrocarbon-substituted succinic acids and the halides, the esters, and the anhydrides thereof having at least about 50 aliphatic carbon atoms in the hydrocarbon substitutent (B) at least about 1 mole of a boron reactant selected from the class consisting of boron oxide, boron halides, boron acids, ammonium salts of boron acids and esters of boron acids with volatile, monohydric alcohols and esters of boron acids with monohydric phenols.

The polyhydroxy compounds from which the boron-containing esters of this invention are derived include principally polyhydric alcohols and polyhydric phenols. They preferably contain less than about 30 carbon atoms and having from 2 to about 10 hydroxy radicals, preferably from 3 to 6 hydroxy radicals, are especially useful. They are illustrated by, for example, alkylene glycols and poly(oxy-alkylene)glycols such as ethylene glycol, di(ethylene glycol), tri-(ethylene glycol), di(-propylene glycol), tri(butylene glycol), penta (ethylene glycol) and other poly(oxy-alkylene)glycols formed by the condensation of two or more moles of ethylene glycol, propylene glycol, octylene glycol, or a like glycol having up to about 12 carbon atoms in alkylene radical. Other useful polyhydric alcohols include glycerol, pentaerythritol, 2,4-hexanediol, pinacol, erythritol, arabitol, sorbitol, mannitol, 1,2-cyclohexanediol, xylylene glycol, and 1,3,5-cyclohexanetriol. The polyhydric phenols are exemplified by hydroquinone, resorcinol, 4-heptyl-1,2-di-hydroxy-benzene, 1,2-dihydroxynaphthalene, 4-polypropene(molecular weight of 1500)-substituted 1,2-dihydroxy-benzene, 5-methyl-8-decyl-1,2-dihydroxy-naphthalene, and pyrogallol.

Still other polyhydroxy compounds include the monoesters of glycerol, sorbitol, mannitol, or other higher polyhydroxy alcohols, such as mono-acetate of glycerol, monooleate of sorbitol, mono-propionate of mannitol, or the like. Also useful are the interpolymers of an unsaturated alcohol with a copolymerizable olefinic substance such as styrene, vinyl ether, vinyl acetate, isobutene, butadiene, di-vinylbenzene or the like. The interpolymers contain two or more monomeric units derived from the unsaturated alcohol and thus constitute the polyhydric alcohols contemplated for use in the process of this invention. Specific examples of such interpolymers are the copolymer of 5 moles of allyl alcohol and 1 mole of styrene having an average molecular weight of about 2500.

The term "hydrocarbon" used in describing the radical R in the formula of the polyhydroxy compounds designates a radical which is substantially hydrocarbon in character. Thus, the radical may contain inert polar groups provided that such groups are not present in proportions sufficiently large to alter significantly the hydrocarbon character of the radical. The polar groups are exemplified by chloro, bromo, keto, ether, aldehyde, nitro, etc. The upper limit with respect to the proportion of such polar groups in a hydrocarbon radical is usually about 10% based upon the weight of the hydrocarbon portion of the radical. However, in the case of the ether groups such as oxyalkylene or poly-(oxy-alkylene) groups the radical may contain as many as one oxygen atom for each two carbon atoms.

The hydrocarbon-substituted succinic acid-producing compounds useful in preparing the boron-containing esters may be the succinic acids, anhydrides, halides, or esters in which the hydrocarbon substituent contains at least about 50 aliphatic carbon atoms. The sources of the hydrocarbon substituent include principally the high molecular weight substantially saturated petroleum fractions and substantially saturated olefin polymers, particularly polymers of mono-olefins having from 2 to 30 carbon atoms. The especially useful polymers are the polymers of 1-mono-olefins such as ethylene, propene, 1-butene, isobutene, 1-hexene, 1-octene, 2-methyl-1-heptene, 3-cyclohexyl-1-butene, and 2-methyl-5-propyl-1-hexene. Polymers of medial olefins, i.e., olefins in which the olefinic linkage is not at the terminal position, likewise are useful. They are illustrated by 2-butene, 3-pentene, and 4-octene.

Also useful are the interpolymers of the olefins such as those illustrated above with other interpolymerizable olefinic substances such as aromatic olefins, cyclic olefins, and polyolefins. Such interpolymers include, for example, those prepared by polymerizing isobutene with styrene; isobutene with butadiene; propene with isoprene; ethylene with piperylene; isobutene with chloroprene; isobutene with p-methyl styrene; 1-hexene with 1,3-hexadiene; 1-octene with 1-hexene; 1-heptene with 1-pentene; 3-methyl-1-butene with 1-octene; 3,3-dimethyl-1-pentene with 1-hexene; isobutene with styrene and piperylene; etc.

The relative proportions of the mono-olefins to the the other monomers in the interpolymers influence the stability and oil-solubility of the final products derived from such interpolymers. Thus, for reasons of oil-solubility and stability the interpolymers contemplated for use in this invention should be substantially aliphatic and substantially saturated, i.e., they should contain at least about 80%, preferably at least about 95%, on a weight basis, of units derived from the aliphatic mono-olefins and no more than about 5% of olefinic linkages based on the total number of carbon-to-carbon covalent linkages. In most instances, the percentage of olefinic linkages should be less than about 2% of the total number of carbon-to-carbon covalent linkages.

Specific examples of such interpolymers include the copolymer of 95% (by weight) of isobutene with 5% of styrene; the terpolymer of 98% of isobutene with 1% of piperylene and 1% of chloroprene; the terpolymer of 95% of isobutene with 2% of 1-butene and 3% of 1-hexene; the terpolymer of 80% of isobutene with 10% of 1-pentene and 10% of 1-octene; the copolymer of 80% of 1-hexene and 20% of 1-heptene; the terpolymer of 90% of isobutene with 2% of cyclohexene and 8% of propene; and the copolymer of 80% of ethylene and 20% of propene.

Another source of the hydrocarbon radical comprises saturated aliphatic hydrocarbons such as highly refined high molecular weight white oils or synthetic alkanes such as are obtained by hydrogenation of high molecular weight olefin polymers illustrated above or high molecular weight olefinic substances.

The use of olefin polymers having molecular weights of about 750–5000 is preferred. Higher molecular weight olefin polymers having molecular weights from about 10,000 to about 100,000 or higher have been found to impart viscosity index improving properties to the final products of this invention. The use of such higher molecular weight olefin polymers often is desirable. It will be noted that the hydrocarbon substituent in the succinic acid-producing compound likewise may contain inert polar groups. Thus, in this respect, it may be a radical which is substantially hydrocarbon in character such as is referred to in the above description of the hydrocarbon radical R of the polyhydroxy compounds.

The succinic acid-producing compounds useful in the above process are preferably substantially hydrocarbon-substituted succinic acids and anhydrides. These succinic compounds are readily available from the reaction of maleic anhydride with a high molecular weight olefin or a chlorinated hydrocarbon such as the olefin polymer described hereinabove. The reaction involves merely heating the two reactants at a temperature about 100°–200° C. The product from such a reaction is an alkenyl succinic anhydride. The alkenyl group may be hydrogenated to an alkyl group. The anhydride may be hydrolyzed by treatment with water or steam to the corresponding acid. Either the anhydride or the acid may be converted to the corresponding acid halide or ester by reaction with, e.g., phosphorus halide, phenols, or alcohols.

In lieu of the olefins or chlorinated hydrocarbons, other hydrocarbons containing an activating polar substitutent, i.e., a substituent which is capable of activating the hydrocarbon molecule in respect to reaction with maleic acid or anhydride, may be used in the above-illustrated reaction for preparing the succinic compounds. Such polar substituents may be illustrated by sulfide, disulfide, nitro, mercaptan, bromine, ketone, or aldehyde radicals. Examples of such polar-substituted hydrocarbons include polypropene sulfide, di-polyisobutene disulfide, nitrated mineral oil, di-polyethylene sulfide, brominated polyethylene, etc. Another method useful for preparing the succinic acids and anhydrides involves the reaction of itaconic acid with a high molecular weight olefin or a polar-substituted hydrocarbon at a temperature usually within the range from about 100° C to about 200° C.

The acid halides of the succinic acids can be prepared by the reaction of the acids or their anhydrides with a halogenation agent such as phosphorus tri-bromide, phosphorus pentachloride or thionyl chloride.

The esters of such acids can be prepared simply by the reaction of the acids or their anhydrides with an alcohol or a phenolic compound such as methanol, ethanol, octadecanol, cyclohexanol, phenol, naphthol, octylphenol, etc. The esterification is usually promoted by the use of an alkaline catalyst such as sodium hydroxide or sodium alkoxide or an acidic catalyst such as sulfuric acid. The nature of the alcoholic or phenolic portion of the ester radical appears to have little influence on the utility of such ester as reactant in the process described hereinabove.

The boron compounds useful as the reactant in the above process include boron oxide, boron oxide hydrate, boron trifluoride, boron tribromide, boron trichloride, boron acids such as boronic acid (e.g., alkyl-$B(OH)_2$ or aryl-$B(OH)_2$), boric acid, (i.e., $H_3BO_3$), tetraboric acid (i.e., $H_2B_4O_7$), metaboric acid (i.e., $HBO_2$), ammonium salts of boron acids, and esters of boron acids with volatile, monohydric alcohols and esters of boron acids with monohydric phenols. The use of complexes of a boron trihalide with esters, ammonia, organic acids, inorganic acids, or hydrocarbons is a convenient means of introducing the boron reactant into the reaction mixture. Such complexes are known and are exemplified by boron trifluoridediethyl ether, boron trifluoride-phenol, boron trifluoride-phosphoric acid, boron trichloride-chloroacetic acid, boron tribromide-dioxane, and boron trifluoride-methyl ethyl ether.

Specific examples of boronic acids include methyl boronic acid, phenyl boronic acid, cyclohexyl boronic acid, p-heptylphenyl boronic acid and dodecyl boronic acid, di-heptylphenyl boronic acid, polyisobutene (molecular weight of 3000)-substituted phenyl boronic acid, and naphthyl boronic acid.

The boron acid esters include especially mono-, di-, and tri-organic esters of boric acid with volatile monohydric alcohols or phenols such as, e.g., methanol, ethanol, isopropanol, cyclohexanol, cyclopentanol, 1-octanol, 2-octanol, 2-butyl cyclohexanol, and other monohydric alcohols preferably boiling below about 150° C. Lower monohydric alcohols, those having less than about 6 carbon atoms, are especially useful for preparing the boric acid ester reactants for the purpose of this invention. Monohydric phenols include phenol, o-cresol, p-cresol and m-cresol.

Methods for preparing the esters of boron acid are known and disclosed in the art (such as "Chemical Reviews" pages 959–1064, Volume 56). Thus, one method involves the reaction of boron trichloride with 3 moles of an alcohol to result in a tri-organic borate. Another method involves the reaction of boric oxide with an alcohol. Another method involves the direct esterification of tetra boric acid with 3 moles of an alcohol.

The ammonium salts of boron acids include principally the salts of boric acid with ammonia or lower alkylamines, i.e., mono-, di-, or tri-alkyl amines having less than 12 carbon atoms in each alkyl radical. Salts of ammonia or such amines with any other boron acid illustrated above are also useful. It is often desirable to use a mixture of an ammonium salt and at least a molar amount of water. Water tends to cause at least partial hydrolysis of the salt, so as to liberate a boron acid. Thus, the use of a mixture of an ammonium salt and water in many instances is an expedient method of introducing a boron acid into the reaction mixture. Specific examples of the ammonium salts are ammonium salt of boric acid; a mixture of one mole of ammonium salt of boric acid and three moles of water; a mixture of one mole of mono-methylamine salt of boric acid and one mole of water; trimethylamine salt of boric acid; di-cyclo-hexylamine salt of boric acid, etc.

The reaction by which the boron-containing esters of this invention are obtained may be carried out by mixing the polyhydric compound, the hydrocarbon-substituted succinic acid-producing compound, and the boron acid-producing compound at a temperature above about 100° C. preferably between about 125° C and 250° C. The optimum reaction temperature depends to some extent upon the nature of the specific reactants used. For instance, where the succinic acid-producing compound and the boron acid-producing compound are relatively reactive acids or anhydrides, the reaction temperature may be below about 200° C. On the other hand, if the acid-producing reactants are esters such as the dimethyl esters of hydrocarbon substituted succinic acids and triphenyl esters of boric acid, the reaction temperature often will be 200° C or higher. The maximum temperature for the process is determined by the decomposition point of the reaction mixture. It rarely exceeds 300° C. In many instances, it is convenient to carry out the reaction in the presence of an inert solvent such as mineral oil, benzene, naphtha, chlorobenzene, etc. The function of the solvent is to facilitate mixing of the reactants and temperature control, and can be easily removed by any ordinary means from the resulting product. For example the boron-containing ester formed by the reaction carried out in the presence of a solvent may be isolated by precipitation or extraction or such known technique. Alternatively, the solvent may be evaporated or removed by vacuum distillation. In the case of mineral oil as solvent, the product may be isolated by adding a non-solvent to the product mixture, so as to precipitate the boron-containing ester from the solvent.

The product resulting from the process of this invention is a complex mixture of esters derived from the polyhydroxy reactant by the esterification of at least one of its hydroxy groups with the succinic acid-producing compound and at least another hydroxy group with the boron reactant. Thus, the product of this invention is a complex mixture of esters characterized by the presence of ester radicals of both succinic acid ester type and boron acid ester type. The precise composition of the product is not fully understood. Consequently, the product is best described in terms of the process by which it is formed.

The composition of the product of this invention depends to a large extent upon the relative proportions of the reactants used in the process. Based upon the stoichiometry of the esterification, at least 0.5 mole of the succinic reactant and at least one mole of the boron reactant are to be used for each mole of the polyhydroxy reactant. Also, the total amounts of the succinic reactant and the boron reactant usually range from about two moles to as many moles as the number of the hydroxy radicals present within the molecular structure of the polyhydroxy reactant. The preferred amounts of the three reactants are such that one mole of the polyhydroxy reactant is used with at least about one mole of the succinic reactant and at least about one mole of the boron reactant and that the molar ratio of the succinic reactant to the boron reactant is within the range of from about 5:1 to 1:5. A specific example of the products of this invention is one obtained by the reaction of one mole of sorbitol with from about 1 to 5 moles of a succinic anhydride and from about 1 to 5 moles of boric acid.

It will be noted that where a reactant is a mixture of two or more individual compounds such as are exemplified by commercial polyhydric alcohols comprising a mixture of tri-, tetra-, penta-, or higher polyhydric alcohols, the average molecular weight may be estimated from the elemental analysis of the mixture. Similarly, in the case of a hydrocarbon-substituted succinic anhydride wherein the hydrocarbon substituent is derived from a mixture of, e.g., olefin polymers, the molecular weight is estimated from the acidity or potential acidity of the anhydride, i.e., it is taken to be twice the equivalent weight based upon the acid number as determined by a standard procedure for determining the acidity of carboxylic acids or anhydrides. The molecular weight of a succinic acid ester likewise may be estimated from the potential acidity as determined by its saponification number. It will be further noted that the upper limit of the number of moles for the combined quantities of the two acid-producing reactants per mole of the polyhydroxy reactant having a particular number of hydroxy groups is based upon the stoichiometry for an esterification involving all of the hydroxy groups of the polyhydroxy reactant. Also, if a stoichiometric excess of a reactant is used, the excess may be present in the product as a diluent.

A preferred mode of carrying out the process of this invention involves reacting a polyhydroxy reactant with the succinic acid-producing reactant to form a partially esterified intermediate and then reacting the intermediate with a boron reactant. When the process is carried out in this manner the first step, i.e., the formation of the partially esterified intermediate, is preferably effected at a temperature between about 100° C and 200° C and the second step, i.e. the reaction of the intermediate with the boron reactant, may be carried out at a temperature from about 80° C to about 250° C. This particular mode of carrying out the process of this invention is preferred because the products resulting therefrom have been found to be especially useful for the purpose of this invention such as in hydrocarbon oil and lubricating compositions.

Another alternative mode of carrying out the process of this invention involves first reacting the polyhydroxy reactant with a boron acid-producing reactant to form a partially esterified intermediate and then reacting the intermediate with the succinic acid-producing reactant.

In this regard, the process admits of further variations in forming the intermediate of a polyhydroxy substance which has been partially esterified with a boron acid. Thus, for instance, the reaction of boric acid with an epoxide, particularly an alkylene oxide such as ethylene oxide, propylene oxide, hexylene oxide, or epichlorohydrin may result in a partially esterified glycol, i.e., a glycol having one free hydroxy group and one hydroxy group which has been converted to a boron acid ester group by esterification with boric acid.

In some instances the formation of the boron-containing esters by the process of this invention is facilitated by the presence in the process of an esterification catalyst. The well-known esterification catalysts are useful for this purpose. They are illustrated by titanium tetrachloride, aluminum chloride, titanium tetrafluoride, boron trifluoride, aluminum tribromide, potassium ethoxide, sodium methoxide, calcium phenate, sodium hydroxide, calcium oxide, benzene sulfonic acid, toluene sulfonic acid, etc. A small amount such as 0.001% by weight of the catalyst often is sufficient to promote esterification of the process of this invention. The amount of the catalyst may range up to about 1% by weight of the process mixture.

It will be appreciated that the reaction of a succinic acid ester or a boron acid ester with a polyhydroxy reactant is a transesterification, i.e., the replacement of an ester radical derived from the polyhydroxy reactant for the ester radical originally present in the succinic or boron acid ester reactant. For instance, where a dimethyl ester of a succinic acid is reacted with a partially esterified glycerol formed by the reaction of glycerol with boric acid, the product of this invention is formed by trans-esterification wherein one or both of the methyl radicals of the succinic reactant are replaced with radicals derived from the partially esterified glycerol intermediate and methanol is the by-product. When tributyl borate is used in the reaction with a partially esterified glycerol formed by the reaction of glycerol and a polyisobutene-substituted succinic acid, the product of this invention is formed by trans-esterification wherein one or more of the butyl radicals of tributyl borate are replaced with the ester radicals derived from the partially esterified glycerol intermediate and butanol is the by-product. The latter may involve trans-esterification reactions including, e.g., the one illustrated as follows:

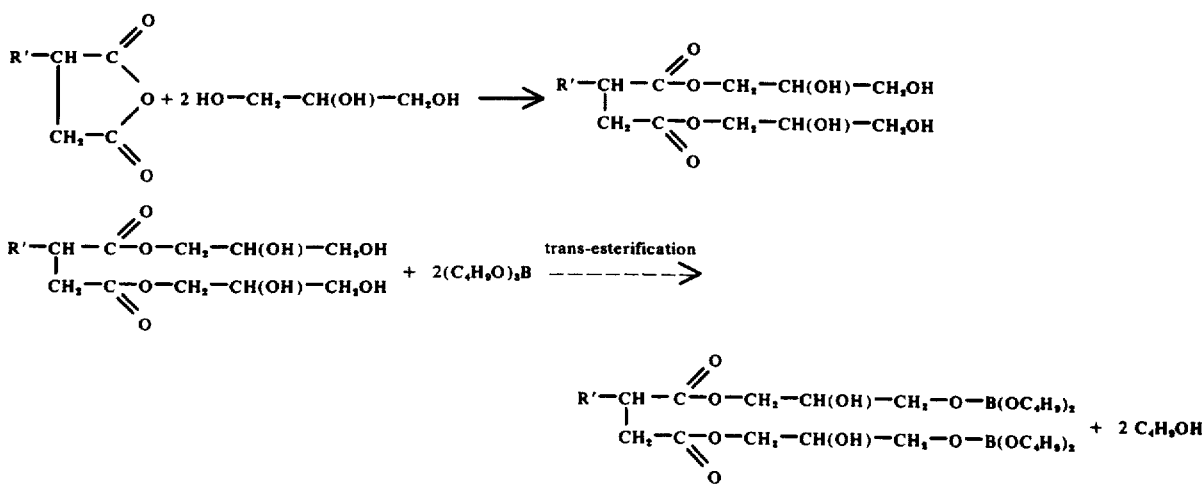

wherein R' is a substantially hydrocarbon radical. The above boron containing ester may react further with the partially esterified glycerol to form more complex products such as polymeric substances. Similarly, the use of a succinic halide (such as a polyisobutene-substituted succinic acid dichloride) or a boron halide (such as boron trifluoride) with a partially esterified polyhydroxy intermediate results in replacing the halide radical of the reactant with an ester radical derived from the partially esterified polyhydroxy intermediate. For instance, the reaction of a succinic dichloride with ethylene glycol and boron oxide may proceed as follows:

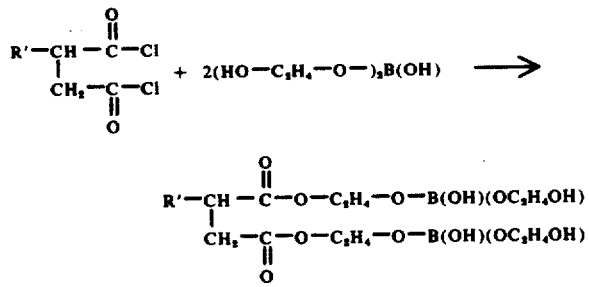

The following examples illustrate the process of this invention.

EXAMPLE 1

An intermediate is obtained by heating 238 grams (1.75 moles) of pentaerythritol and 1940 grams (1.75 moles) of a polyisobutene-substituted succinic anhydride (having an acid number of 100 and prepared by the reaction of maleic anhydride with a chlorinated polyisobutene having a chlorine content of 4.3% and a molecular weight of 1000) in 1430 grams of mineral oil at 150° C for 5 hours and at 200°–210° C for 5 more hours and then filtering the residue. To 520 grams of the filtrate there is added 15.5 grams (1 mole per mole of the pentaerythritol used) of boric acid. The resulting mixture is heated at 145° C for 2 hours and at 160°–165° C for 1 hour whereupon water is distilled off. The residue is filtered. The filtrate is an oil solution of the desired ester and has a boron content of 0.5%.

EXAMPLE 2

To 544 grams (0.5 mole) of the polyisobutene-substituted succinic anhydride of Example 1 and 417 grams of mineral oil, there is added at 110°–115° C in 10 minutes 96 grams (0.5 mole) of sorbitol. The mixture is blown with nitrogen at 150°–155° C for 3 hours. To this mixture there is added 31 grams (0.5 mole) of boric acid at 140°–150° C in 20 minutes. The resulting mixture is heated at 150°–155° C for 1 hour and then blown with nitrogen at 200° C for 3 hours. The residue is filtered. The filtrate is a 40% oil solution of the desired ester and has a boron content of 0.23%.

EXAMPLE 3

A mixture of 594 grams of mineral oil, 358 grams (0.76 mole) of sorbitol monooleate, and 544 grams (0.5 mole) of the polyisobutene-substituted succinic anhydride of Example 1 is heated at 150° C for 4 hours and filtered. The filtrate is an ester intermediate having a saponification number of 76 and a hydroxyl content of 1.1%. To 540 grams of the filtrate there is added 27 grams of boric acid at 150° C in 10 minutes. The residue is blown with nitrogen at 150° C for 3.5 hours and then filtered. The filtrate has a boron content of 0.5%.

EXAMPLE 4

A mixture of 544 grams (0.5 mole) of the polyisobutene-substituted succinic anhydride of Example 1, 182 grams (1 mole) of boric acid, and 476 grams of mineral oil is blown with nitrogen at 200°–210° C for 3 hours and then mixed with 62 grams (1 mole) of boric acid at 200°–210° C for 3 hours. The resulting mixture is filtered. The filtrate is a 40% oil solution of the desired ester and has a boron content of 0.5% and a saponification number of 59.

EXAMPLE 5

The polyisobutene-substituted succinic anhydride of Example 1, 1632 grams (1.5 moles), and a commercial polyoxyethylene sorbitol monooleate (1590 grams, 1.25 moles; prepared by treating sorbitol monooleate with 20 moles ethylene oxide) in 600 grams of toluene is heated at 109°–142° C for 12 hours and then to 150° C/9 mm to distill off volatile components. The residue is diluted with 1324 grams of mineral oil, mixed with a filter aid and filtered. The filtrate is a partially esterified intermediate having a hydroxyl content of 0.4 and a saponification number of 54. To 950 grams of this intermediate and 175 grams of mineral oil there is added 10 grams of boric acid (one boron radical per each hydroxyl radical). The mixture is blown with nitrogen at 150° C for 3 hours and filtered. The filtrate has a boron content of 0.2%.

EXAMPLE 6

A mixture of 1 mole of ethylene glycol, 1 mole of boric acid, and 1 mole of a 40% mineral oil solution of a polypropene (molecular weight of 1500)-substituted succinic acid is prepared at room temperature and then heated at 150° C for 7 hours whereupon water is distilled off. The residue is the desired ester.

EXAMPLE 7

A mixture of 2000 grams of mineral oil, 1 mole of glycerol, 1 mole of boric oxide, and 1.5 moles of dimethyl ester of a succinic acid obtained by the reaction of maleic anhydride with a copolymer of 95 parts (by weight) of isobutene and 5 parts of styrene having a molecular weight of 1000 is prepared at 50° C and then heated at 200° C for 5 hours whereupon water and methyl alcohol are distilled off as the by-products. The residue is filtered. The filtrate is an oil solution of the desired ester.

EXAMPLE 8

An intermediate is obtained by heating a mixture of 1 mole of boron trifluoride and 1 mole of 1,2-octylene glycol at 80°–120° C. The intermediate is mixed with an equal volume of dioxane and then with a 60% mineral oil solution of a polyisobutene (molecular weight of 60.000) substituted succinic anhydride. The resulting mixture is heated at reflux for 5 hours and then heated to 210° C/2 mm. The residue is filtered. The filtrate is an oil solution of the desired ester.

EXAMPLE 9

Resorcinol (1 mole) is added at 120° C to a mixture of 1 mole of boric acid and 1 mole of a polyethylene (molecular weight 1000)-substituted succinic anhydride. The resulting solution is mixed with an equal volume of mineral oil and heated at 120° C–150° C for 8 hours and filtered. The residue is filtered and the filtrate is an oil solution of the desired ester.

EXAMPLE 10

An intermediate is obtained by heating at 120°–180° C, 1 mole of ammonium borate, 1 mole of water, 1 mole of a copolymer (molecular weight of 1100) of styrene and allyl alcohol (molar ratio of 1 to 5). To this intermediate there is added a 80% mineral oil solution of a succinic anhydride obtained by reacting at 200° C 1.2 moles of maleic anhydride with 1 mole of a copolymer (molecular weight of 2000) of 98 parts (by weight) of isobutene and 2 parts of isoprene. The resulting mixture is heated at 150°–220° C and filtered. The filtrate is an oil solution of the desired ester.

EXAMPLE 11

An intermediate is obtained by heating 1.75 moles of pentaerythritol and 1.75 moles of a polyisobutene(-molecular weight 1000)-substituted succinic anhydride at 150°–200° C. To one mole of the intermediate, there is added one mole of boric acid and the resulting mixture is heated at 150°–200° C, whereupon water is distilled off. The residue is decanted and the filtrate is the desired boron-containing ester.

EXAMPLE 12

The process of Example 11 is carried out in the presence of 1000 cc of xylene as the solvent (added during the preparation of the intermediate). At the end of the reaction, the solvent is evaporated by vacuum distillation.

The boron-containing esters of this invention are useful for a wide variety of purposes including pesticides, plasticizers, rust-inhibiting agents for treatment of metals, corrosion-inhibiting agents, extreme pressure agents, antiwear agents, and detergents.

A principal utility of such products is as additives in lubricants. It has been discovered in accordance with this invention that when used for such purpose their effectiveness to impart a specific property to a lubricant is closely related to the size of the hydrocarbon substituent in the hydrocarbon-substituted succinic acid-producing compounds from which the boron-containing esters are derived. More particularly it has been found that products in which the substantially hydrocarbon substituent contains more than about 50 aliphatic carbon atoms are particularly effective for the purposes of this invention.

The lubricating oils in which the boron-containing esters of this invention are useful as additives may be of synthetic, animal, vegetable, or mineral origin. Ordinarily mineral lubricating oils are preferred by reason of their availability, general excellence, and low cost. For certain applications, oils belonging to one of the other three groups may be preferred. For instance, synthetic polyester oils such as didodecyl adipate and di-2-ethylhexyl sebacate are often preferred as jet engine lubricants. Normally the lubricating oils preferred will be fluid oils, ranging in viscosity from about 40 Saybolt Universal Seconds at 100° F to about 200 Saybolt Universal Seconds at 210° F.

The concentration of the boron-containing esters as additives in lubricants usually ranges from about 0.01% to about 15% by weight. The optimum concentrations for a particular application depend to a large measure upon the type of service to which the lubricant is to be subjected. Thus, for example, lubricants for use in gasoline internal combustion engines may contain from about 0.5 to about 10% of the additive, whereas lubricating compositions for use in gears and diesel engines may contain as much as 20% or even more of the additive. Lubricants for use in the oil-fuel mixture for two-stroke engines may contain from about 1% to 10% of the additive.

This invention contemplates also the presence of other additives in the lubricating compositions. Such additives include, for example, supplemental detergents of the ash-containing type, viscosity index improving agents, pour point depressing agents, anti-foam agents, extreme pressure agents, rust-inhibiting agents, and supplemental oxidation and corrosion-inhibiting agents.

The ash-containing detergents are exemplified by oil-soluble neutral and basic salts of alkali or alkaline earth metals with sulfonic acids, carboxylic acids, or organic phosphorus acids characterized by at least one direct carbon-to-phosphorus linkage such as those prepared by the treatment of an olefin polymer (e.g., polyisobutene having a molecular weight of 1000) with a phosphorizing agent such as phosphorus trichloride, phosphorus heptasulfide, phosphorus pentasulfide, phosphorus trichloride and sulfur, white phosphorus and a sulfur halide, or phosphorothioic chloride. The most commonly used salts of such acids are those of sodium, potassium, lithium, calcium, magnesium, strontium, and barium.

The term "basic salt" is used to designate the metal salts wherein the metal is present in stoichiometrically larger amounts than the organic acid radical. The commonly employed methods for preparing the basic salts involves heating a mineral oil solution of an acid with a stoichiometric excess of a metal neutralizing agent such as the metal oxide, hydroxide, carbonate, bicarbonate, or sulfide at a temperature about 50° C and filtering the resulting mass. The use of a promoter in the neutralization step to aid the incorporation of a large excess of metal likewise is known. Examples of compounds useful as the promoters include phenolic substances such as phenol, naphthol, alkylphenol, thiophenol, sulfurized alkylphenol, and condensation products of formaldehyde with a phenolic substance; alcohols such as methanol, 2-propanol, octyl alcohol, cellosolve, carbitol, ethylene glycol, stearyl alcohol, and cyclohexyl alcohol; amines such as aniline, phenylenediamine, phenothiazine, phenyl beta-naphthylamine, and dodecylamine. A particularly effective method for preparing the basic salts comprises mixing an acid with an excess of a basic alkaline earth metal neutralizing agent, a phenolic promoter compound, and a small amount of water and carbonating the mixture at an elevated temperature such as 60°–200°C.

The preparation of a basic sulfonate detergent is illustrated as follows: A mixture of 490 parts (by weight) of a mineral oil, 110 parts of water, 61 parts of heptylphenol, 340 parts of barium mahogany sulfonate, and 227 parts of barium oxide is heated at 100°C for 0.5 hour and then to 150°C. Carbon dioxide is then bubbled into the mixture until the mixture is substantially neutral. The mixture is filtered and the filtrate found to have a sulfate ash content of 25%.

The preparation of a basic barium salt of a phosphorus acid is illustrated as follows: A polyisobutene having a molecular weight of 50,000 is mixed with 10% by weight of phosphorus pentasulfide at 200°C for 6 hours. The resulting product is hydrolyzed by treatment with steam at 160°C to produce an acidic intermediate. The acidic intermediate is then converted to a basic salt by mixing twice its volume of mineral oil, 2 moles of barium hydroxide and 0.7 mole of phenol and carbonating the mixture at 150°C to produce a fluid product.

The phosphorus-containing esters are especially adapted for used in combination with extreme pressure and corrosion-inhibiting additives such as metal dithiocarbamates, xanthates, the Group II metal phosphorodithioates and their epoxid adducts, hindered phenols, sulfurized cycloalkanes, dialkyl polysulfides, sulferized fatty ester, phosphosulfurized fatty ester, alkaline earth metal salts of alkylated phenols, dialkyl phophites, triaryl phosphites, and esters of phosphorodithioic acids. Combinations of the phosphorus-containing esters of this invention with any of the above-mentioned additives are especially desirable for use in lubricants which must have superior extreme pressure and oxidation-inhibiting characteristics.

The Group II metal phosphorodithioates are the salts of acids having the formula

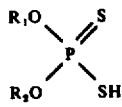

in which $R_1$ and $R_2$ are substantially hydrocarbon radicals. The metals for forming such salts are exemplified by barium, calcium, strontium, zinc, and cadmium. The barium and zinc phosphorodithioates are especially preferred. The substantially hydrocarbon radicals in the phosphorodithioic acid are preferably low or medium molecular weight alkyl radicals and alkylphenyl radicals, i.e., those having from about 1 to about 30 carbon atoms in the alkyl group. Illustrative alkyl radicals include methyl, ethyl, isopropyl, isobutyl, n-butyl, sec-butyl, the various amyl alcohols, n-hexyl, methylisobutyl carbinyl, heptyl, 2-ethylhexyl, diisobutyl, isooctyl, nonyl, behenyl, decyl, etc. Illustrative lower alkylphenyl radicals include butylphenyl, amylphenyl, di-amylphenyl, octylphenyl, etc. Cycloalkyl radicals likewise are useful and these include chiefly cyclohexyl and the lower alkylcyclohexyl radicals. Other substantially hydrocarbon radicals likewise are useful such as tetradecyl, octadecyl, eicosyl, butylnaphthyl, hexyl-naphthyl, octylnaphthyl, cyclohexylphenyl, naphthenyl, etc. Many substituted hydrocarbon radicals may also be used, e.g., chloropentyl, dichlorophenyl, and dichlorodecyl.

The availability of the phosphorodithioic acides from which the Group II metal salts of this invention are prepared is well know. They are prepared by the reation of phosphorus pentasulfide with an alcohol or phenol. The reaction involves four moles of the alcohol or phenol per mole of phosphorus pentasulfide, and may be carried out within the temperature range from about 50° C to about 200° C. Thus the preparation of O,O-di-n-hexyl phosphorodithioic acid involves the reaction of phosphorus pentasulfide with four moles of n-hexyl alcohol at about 100° C for about 2 hours. Hydrogen sulfide is liberated and the residue is the defined acid. The preparation of the zinc or barium salt of this acid may be effected by reaction with zinc oxide or barium oxide. Simply mixing and heating these two reactants is sufficient to cause the reaction to take place and the resulting product is sufficiently pure for the purposes of this invention.

Especially useful Group II metal phosphorodithioates can be prepared from phosphorodithioic acids which in turn are prepared by the reaction of phosphorus pentasulfide with mixtures of alcohols. The use of such mixtures enables the utilization of cheaper alcohols which in themselves do not yield oil-soluble phosphordithioic acids. Thus a mixture of isopropyl and hexyl alcohols can be used to produce a very effective, oil-soluble metal phosphorodithioate. For the same reason mixtures of simple phosphorodithioic (i.e., acids prepared from one alcohol) acids can be reacted with zinc oxide or barium oxide to produce less expensive, oil-soluble salts.

Another class of the phosphorothioate additives contemplated for use in the lubricating compositions of this invention comprises the adducts of the metal phosphorodithioates described above with an epoxide. The metal phosphorodithioates useful in preparing such adducts are for the most part the zinc phosphorodithioates. The epoxides may be alkylene oxides or arylalkylene oxides. The arylalkylene oxides are exemplified by styrene oxide, p-ethylstyrene oxide, alpha-methylstyrene oxide, 3-beta-naphthyl-1,3-butylene oxide, m-dodecylstyrene oxide, and p-chlorostyrene oxide. The alkylene oxides include principally the lower alkylene oxides in which the alkylene radical contains 6 or less carbon atoms. Examples of such lower alkylene oxides are ethylene oxide, propylene oxide, 1,2-butene oxide, trimethylene oxide, tetramethylene oxide, butadiene monoepoxide, 1,2-hexene oxide, and propylene epichlorohydrin. Other epoxides useful herein include, for example, butyl 9,10-epoxy-stearate, epoxidized soya bean oil, epoxidized tung oil, and epoxidized copolymer of styrene with butadiene.

The adduct may be obtained by simply mixing the phosphorodithioate and the epoxide. The reaction is usually exothermic and may be carried out within wide temperature limits from about 0° C to about 200° C. Because the reaction is exothermic it is best carried out by adding one reactant, usually the epoxide, in small increments to the other reactant in order to obtain convenient control of the temperature of the reaction. The reaction may be carried out in a solvent such as benzene, mineral oil, naphtha, or n-hexane.

The chemical structure of the adduct is not known. More than one mole, sometimes as many as four moles, of the epoxide can be made to combine with the phosphorodithioate to form products useful herein. However, adducts obtained by the reaction of one mole of the phosphorodithioate with from about 0.25 mole to about 1 mole of a lower alkylene oxide, particularly ethylene oxide and propylene oxide, have been found to be especially useful and therefore are preferred.

The lubricating compositions may contain metal detergent additives in amounts usually within the range of about 0.1% to about 20% by weight. In some applications such as in lubricating marine diesel engines the lubricating compositions may contain as much as 30% of a metal detergent additive. They may contain other additives such as extreme pressure addition agents, viscosity index improving agents, and pour point depressing agents, each in amounts within the range from about 0.1% to about 10%.

The following examples are illustrative of the lubricating compositions of this invention: (all percentages are by weight).

EXAMPLE I

SAE 20 mineral lubricating oil containing 0.5% of the product of Example 1.

EXAMPLE II

SAE 30 mineral lubricating oil containing 0.75% of the product of Example 2 and 0.1% of phosphorus as the barium salt of di-n-nonylphosphorodithioic acid.

EXAMPLE III

SAE 10W-30 mineral lubricating oil containing 0.4% of the product of Example 3.

EXAMPLE IV

SAE 90 mineral lubricating oil containing 0.1% of the product of Example 4 and 0.15% of the zinc salt of an equimolar mixture of di-cyclohexylphosphorodithioic acid and di-isobutyl phosphorodithioic acid.

EXAMPLE V

SAE 30 mineral lubricating oil containing 2% of the product of Example 4.

EXAMPLE VI

SAE 20W-30 mineral lubricating oil containing 5% of the product of Example 5.

EXAMPLE VII

SAE 10W-30 mineral lubricating oil containing 1.5% of the product of Example 2 and 0.05% of phosphorus as the zinc salt of a phosphorus as the zinc salt of a phosphorodithioic acid prepared by the reaction of phosphorus pentasulfide with a mixture of 60% (mole) of p-butylphenol and 40% (mole) of n-pentyl alcohol.

EXAMPLE VIII

SAE 50 mineral lubricating oil containing 3% of the product of Example 4 and 0.1% of phosphorus as the calcium salt of di-hexylphosphorodithioate.

EXAMPLE IX

SAE 10W-30 mineral lubricating oil containing 2% of the product of Example 2, 0.06% of phosphorus as zinc di-n-octylphosphorodithioate, and 1% of sulfate ash as barium mahogany sulfonate.

EXAMPLE X

SAE 30 mineral lubricating oil containing 5% of the product of Example 10, 0.1% of phosphorus as the zinc salt of a mixture of equimolar amounts of di-isopropylphosphorodithioic acid and di-n-decylphosphorodithioic acid, and 2.5% of sulfate ash as a basic barium detergent prepared by carbonating at 150° C a mixture comprising mineral oil, barium di-dodecylbenzene sulfonate and 1.5 moles of barium hydroxide in the presence of a small amount of water and 0.7 mole of octylphenol as the promoter.

EXAMPLE XI

SAE 10W-30 mineral lubricating oil containing 6% of the product of Example 7, 0.075% of phosphorus as zinc di-n-octylphosphorodithioate, and 5% of the barium salt of an acidic composition prepared by the reaction of 1000 parts of a polyisobutene having a molecular weight of 60,000 with 100 parts of phosphorus pentasulfide at 200° C and hydrolyzing the product with steam at 150° C.

EXAMPLE XII

SAE 10 mineral lubricating oil containing 2% of the product of Example 8, 0.075% of phosphorus as the adduct of zinc di-cyclohexylphosphorodithioate treated with 0.3 mole of ethylene oxide, 2% of a sulfurized sperm oil hving a sulfur content of b 10%, 3.5% of a poly-(alkyl methacrylate) viscosity index improver, 0.02% of poly-(alkyl methacrylate) pour point depressant, 0.003% of a poly-(alkyl siloxane) anti-foam agent.

EXAMPLE XIII

SAE 10 mineral lubricating oil containing 1.5% of the product of Example 9, 0.075% of phosphorus as the adduct obtained by heating zinc dinonylphosphorodithioate with 0.25 mole of 1,2-hexene oxide at 120° C, a sulfurized methyl ester of tall oil cid having a sulfur content of 15%, 6% of a polybutene viscosity index improver 0.005% of a poly-(alkyl methacrylate) anti-foam agent, and 0.5% of lard oil.

EXAMPLE XIV

SAE 20 mineral lubricating oil containing 1.5% of the product of Example 2, 0.5% of di-dodecyl phosphite, 2% of the sulfurized sperm oil having a sulfur content of 9%, a basic calcium detergent prepared by carbonating a mixture comprising mineral oil, calcium mahogany sulfonate and 6 moles of calcium hydroxide in the presence of an equi-molar mixture (10% of the mixture) of methyl alcohol and n-butyl alcohol as the promoter at the reflux temperature.

EXAMPLE XV

SAE 10 mineral lubricating oil containing 25% of the product of Example 3, 0.07% of phosphorus as zinc di-octylphosphorodithioate, b 2% of a barium detergent prepared by neutralizing with barium hydroxide the hydrolyzed reaction product of a polypropylene (molecular weight 2000) with 1 mole of phosphorus pentasulfide and 1 mole of sulfur, 3% of a barium sulfonate detergent prepared by carbonating a mineral oil solution of mahogany acid, and a 500% stoichiometrically excess amount of barium hydroxide in the presence of phenol as the promoter at 180° C, 3% of a supplemental ashless detergent prepared by copolymerizing a mixture of 95% (weight) of decyl-methacrylate and 5% (weight) of diethylaminoethylacrylate.

EXAMPLE XVI

SAE 30 mineral lubricating oil containing 2% of the product of Example 5, 0.1% of phosphorus as zinc di-n-hexylphosphorodithioate, 10% of a chlorinated paraffin wax having a chlorine content of 40%, 2% of di-butyl tetrasulfide, 2% of sulfurized dipentene, 0.2% of oleyl amide, 0.003% of an anti-foam agent, 0.02% of a pour point depressant, and 3% of a viscosity index improver.

EXAMPLE XVII

SAE 10 mineral lubricating oil containing 3% of the product of Example 3, 0.075% of phosphorus as the zinc salt of a phosphorodithioic acid prepared by the reaction of phosphorus pentasulfide with an equimolar mixture of n-butyl alcohol and dodecyl alcohol, 3% of a barium detergent prepared by carbonating a mineral oil solution containing 1 mole of sperm oil, 0.6 mole of octylphenol, 2 moles of barium oxide, and a small amount of water at 150° C.

EXAMPLE XVIII

SAE 20 mineral lubricating oil containing 2% of the product of Example 10 and 0.07% of phosphorus as zinc di-n-octylphosphorodithioate.

EXAMPLE XIX

SAE 30 mineral lubricating oil containing 3% of the product of Example 4 and 0.1% of phosphorus as zinc di-(isobutylphenyl)-phosphorodithioate.

EXAMPLE XX

SAE 50 mineral lubricating oil containing 2% of the product of Example 5.

EXAMPLE XXI

SAE 90 mineral lubricating oil containing 3% of the product of Example 4 and 0.2% of phosporus as the reaction product of 4 moles of turpentine with 1 mole of phosphorus pentasulfide.

EXAMPLE XXII

SAE 90 mineral lubricating oil containing 3% of the production of Example 2 and 0.2% of 4,4'-methylene-bis(2,6-tertbutylphenol).

EXAMPLE XXIII

SAE 30 mineral lubricating oil containing 2% of the product of Example 3 and 0.1% of phosphorus as phenylethyl dicyclohexylphosphorodithioate.

EXAMPLE XXIV

SAE 90 mineral lubricating oil containing 5% of the product of Example 1 and 1% of the calcium salt of the sulfurized phenol obtained by the reaction of 2 moles of heptylphenol with 1 mole of sulfur.

EXAMPLE XXV

SAE 10W-30 mineral lubricating oil containing 2.5% of the solvent free boron-containing ester of Example 12.

The above lubricants are merely illustrative and the scope of invention includes the use of all the additives previously illustrated as well as others within the broad concept of this invention described herein.

The detergent properties of the boron-containing esters of this invention and the utility thereof as additives in hydrocarbon oil compositions are illustrated by the results from the following detergency test. In this test a mixture of three grams of a synthetic sludge consisting of a carbon black paste (20 parts by weight of carbon black and 80 parts by weight of white oil), 0.3 gram of water, and 77 cc of a kerosene solution containing the additive is homogenized to form a suspension and then allowed to settle at room temperature. The time required for the sediment of carbon black is taken as a measure of the effectiveness of the additive as a detergent, i.e., the longer the time the more effective the additive. By this test a sample without the additive results in the complete sediment of carbon black in less than one day. The same sample containing 0.2% by weight of the product obtained by the reaction of one mole of pentaerythritol with one mole of the polyisobutene-substituted succinic anhydride of Example 1 and 2.8 moles of boric acid (according to the procedure of Example 1) shows no sediment after seven days.

What is claimed is:

1. A process for the preparation of boron-containing esters of a polyhydroxy compound chracterized by the presence of ester radicals of both a succinic acid type and a boron acid type which comprises the esterification of one mole of a polyhydroxy compound having the formula $R(OH)_x$, wherein R represents a hydrocarbon radical and $x$ is an integer having a value of from 2 to about 10, with
   A. at least about 0.5 mole of a hydrocarbon-substituted succinic acid-producing compound selected from the group consisting of the acid, acid halides, esters, and acid anhydrides, wherein the hydrocarbon substituent has at least about fifty aliphatic carbon atoms; and
   B. at least about one mole of a boron-containing reactant selected from the group consisting of boron oxide, boron halides, boron acids, ammonium salts of boron acids, esters of boron acids with volatile monohydric alcohols, wherein the alcohols have boiling points below about 150° C., and esters of boron acids with monohydric phenols;
wherein the total amount of the succinic acid-producing compound of (A) and the boron reactant of (B) to take part in the esterification reaction does not exceed $x$ moles per mole of polyhydroxy compound.

2. The process of claim 1, wherein the hydrocarbon radical of the polyhydroxy compound has a molecular weight of up to about 2500, and may contain up to about ten percent by weight of a polar substituent.

3. The process of claim 1, wherein the hydrocarbon substituent of the hydrocarbon-substituted succinic acid-producing compound has a molecular weight of up to about 100,000, contains no more than about five percent of olefinic linkages based upon the total number of carbon-to-carbon covalent linkages and may contain up to about ten percent by weight of a polar substituent.

4. The process of claim 1, wherein the polyhydroxy compound has up to about 30 carbon atoms and up to 8 hydroxy radicals, the hydrocarbon-substituted succinic acid-producing compound is a succinic anhydride, wherein the hydrocarbon substituent has a molecular weight in the range of from about 750 to about 5000, and the boron-containing reactant is boric acid.

5. The process of claim 1, wherein the hydrocarbon substituent of the hydrocarbon-substituted succcinic anhydride is derived from a polyisobutene.

6. A process for the preparation of boron-containing esters of a polyhydroxy compound characterized by the presence of ester radicals of both a succinic acid type and a boron acid type which comprises the steps of
   1. the partial esterification at a reaction temperature above 100° C. of a polyhydroxy compound corresponding to the formula $R(OH)_x$, wherein R represents a hydrocarbon radical, and $x$ is an integer having a value of from 2 to about 10, with
      A. at least about 0.5 mole of a hydrocarbon-substituted succinic acid-producing compound selected from the group consisting of the acid, acid halides, esters, and anhydrides, wherein the hydrocarbon substituent has at least about fifty carbon atoms;

and 2. the esterification of the intermediate product of step (1) at a temperature above about 100° C., with B. at least about one mole of a boron-containing reactant selected from the group consisting of boron oxide, boron halides, boron acids, ammonium salts of boron acids, esters of boron acids with volatile monohydric alcohols, wherein the alcohols have boiling points below about 150° C., and esters of boron acids with monohydric phenols;

wherein the total amount of the succinic acid-producing compound (A) and the boron-containing reactant (B) to take part in the esterification reaction does not exceed $x$ moles per mole of polyhydroxy compound.

7. A process for the preparation of boron-containing esters of a polyhydroxy compound characterized by the presence of ester radicals of both a succinic acid type and a boron acid type which comprises the steps of 1. the partial esterification at a reaction temperature above about 100° C. of a polyhydroxy compound having up to about 30 carbon atoms and having up to 8 hydroxy radicals, with A. at least about 0.5 mole of a polyisobutene-substituted succinic anhydride, wherein the polyisobutene substituent has a molecular weight in the range of from about 750 to 5000;

and 2. the esterification of the reaction product of step (1) at a temperature above about 100° C., with B. at least about one mole of boric acid; wherein the total number of the hydroxy radicals in the polyhydroxy alcohol is at least as great as the total number of moles of the succinic anhydride and the boric acid.

8. Boron-containing esters of a polyhydroxy compound characterized by the presence of ester radicals of both a succinic acid type and a boron acid type prepared by a process comprising the esterification of one mole of a polyhydroxy compound corresponding to the formula $R(OH)_x$, wherein R is a hydrocarbon radical, and $x$ is an integer having a value of from 2 to about 10, with A. at least about 0.5 mole of a hydrocarbon-substituted succinic acid-producing compound selected from the group consisting of the acid, acid halides, esters, and anhydrides, wherein the hydrocarbon substituent has at least about fifty aliphatic carbon atoms; and B. at least about one mole of a boron-containing reactant selected from the group consisting of boron oxide, boron halides, boron acids, ammonium salts of boron acids, esters of boron acids with volatile monohydric alcohols, wherein the alcohols have boiling points below about 150° C., and esters of boron acids with monohydric phenols;

wherein the total amount of the succinic acid-producing compound of (A) and the boron reactant of (B) to take part in the esterification does not exceed $x$ moles per mole of polyhydroxy compound.

9. The boron-containing esters of claim 8, wherein the hydrocarbon radical of the polyhydroxy compound has a molecular weight of up to about 2500, and may contain up to ten percent by weight of a polar substituent.

10. The boron-containing esters of claim 8, wherein the hydrocarbon substituent of the hydrocarbon-substituted succinic acid-producing compound has a molecular weight of up to about 100,000, and may contain up to about ten percent by weight of a polar substituent.

11. Boron-containing esters of a polyhydroxy compound characterized by the presence of ester radicals of both a succinic acid type and a boron acid type prepared by a process which comprises the steps of 1. the partial esterification at a reaction temperature above 100° C. of a polyhydroxy compound corresponding to the formula $R(OH)_x$, wherein R represents a hydrocarbon radical, and $x$ is an integer having a value of from 2 to about 10, with A. at least about 0.5 mole of a hydrocarbon-substituted succinic acid-producing compound selected from the group consisting of the acid, acid halides, esters, and anhydrides, wherein the hydrocarbon substituent has at least about fifty carbon atoms;

and 2. the esterification of the intermediate of step (1) at a temperature above about 100° C., with B. at least about one mole of a boron-containing reactant selected from the group consisting of boron oxide, boron halides, boron acids, ammonium salts of boron acids, esters of boron acids, with volatile monohydric alcohols, wherein the alcohols have boiling points below about 150° C., and esters of boron acids with monohydric phenols;

wherein the total amount of the succinic acid-producing compound and the boron-containing reactant to take part in the esterification reaction does not exceed $x$ moles per mole of polyhydroxy compound.

* * * * *